United States Patent [19]

Wright

[11] Patent Number: 4,657,010

[45] Date of Patent: Apr. 14, 1987

[54] ADJUSTABLE FACE MASK

[76] Inventor: Stewart L. Wright, 115½ E. Pine St., Altadena, Calif. 91001

[21] Appl. No.: 772,031

[22] Filed: Sep. 3, 1985

[51] Int. Cl.⁴ .................... A61M 16/00; A62B 7/10
[52] U.S. Cl. .................... 128/205.25; 128/206.16; 128/206.24; 128/206.19
[58] Field of Search .................... 2/206, 9, 424; 128/201.23, 201.24, 201.25, 203.29, 205.25, 205.29, 206.12, 206.16, 206.17, 206.19, 206.21, 206.28, 206.24; 446/27

[56] References Cited

U.S. PATENT DOCUMENTS

| D. 250,047 | 10/1978 | Lewis et al. | 128/205.25 |
| 1,224,039 | 4/1917 | Synohubyk | 128/205.29 |
| 2,245,658 | 6/1941 | Erickson | 128/206.28 |
| 2,762,368 | 9/1956 | Bloomfield | 128/206.28 |
| 4,440,163 | 4/1984 | Spengel | 128/205.25 |

FOREIGN PATENT DOCUMENTS

| 7002 | 11/1879 | Fed. Rep. of Germany | 128/206.16 |
| 34762 | 4/1952 | Poland | 128/205.25 |

Primary Examiner—Henry J. Recla
Attorney, Agent, or Firm—Oldham, Oldham & Weber Co.

[57] ABSTRACT

An adjustable mask for supplying a desired atmosphere to the wearer is disclosed. This mask may be either an oxygen mask or a mask for removing dust or pollen. The mask has overlapping upper and lower sections. The area of overlap can be made larger or smaller depending on the facial length of the wearer. The area of overlap is larger for a smaller adult, and smaller for a larger adult. Gripping means, shown herein as snaps and eyelets, are provided on both sections in the area of overlap so that the two sections can be adjustably secured to each other. These gripping means can also consist of velcro or any substance allowing the two mask sections to fit together snugly.

12 Claims, 7 Drawing Figures

ADJUSTABLE FACE MASK

TECHNICAL FIELD

This invention relates to face masks for supplying a desired atmosphere to the wearer such as oxygen masks and masks for removing dust or pollen. More particularly, this invention relates to novel adjustable masks for this type.

BACKGROUND ART

Masks for supplying a desired atmosphere to the wearer, such as oxygen masks and masks for removing dust and pollen, are well known and widely used. A problem is that they seldom fit the wearer properly. This is because such masks typically are provided in only one size. Such masks may fit an adult of average size reasonably well, but they fit poorly on a larger or smaller adult. At best, such a mask is uncomfortable; at worst, its effectiveness is diminished at least somewhat.

DISCLOSURE OF THE INVENTION

The present invention provides masks which can be adjusted to fit the facial dimensions of the wearer. According to this invention, there is provided an adjustable mask for supplying a desired atmosphere to the wearer, which mask comprises upper and lower sections which together are adapted to cover the wearer's face and to form an airtight enclosure therewith, and means for adjustably securing the two sections together in overlapping relationship, said means comprising gripping means carried by at least one of said sections in the portion that overlaps the other, said gripping means being capable of maintaining the two sections in a plurality of different positions relative to each other so that the mask can be made larger or smaller in accordance with the facial dimensions of the wearer. The gripping means preferably comprises first gripping means along the lateral edges of the upper section in the lower portion thereof, and second gripping means, capable of coacting with the first gripping means, along the lateral edges of the lower section in the upper portion thereof.

Two embodiments of the invention are described. The first is an adjustable oxygen mask; the second is an adjustable mask for removing dust or pollen.

BEST MODE FOR CARRYING OUT THE INVENTION

Figure 1:
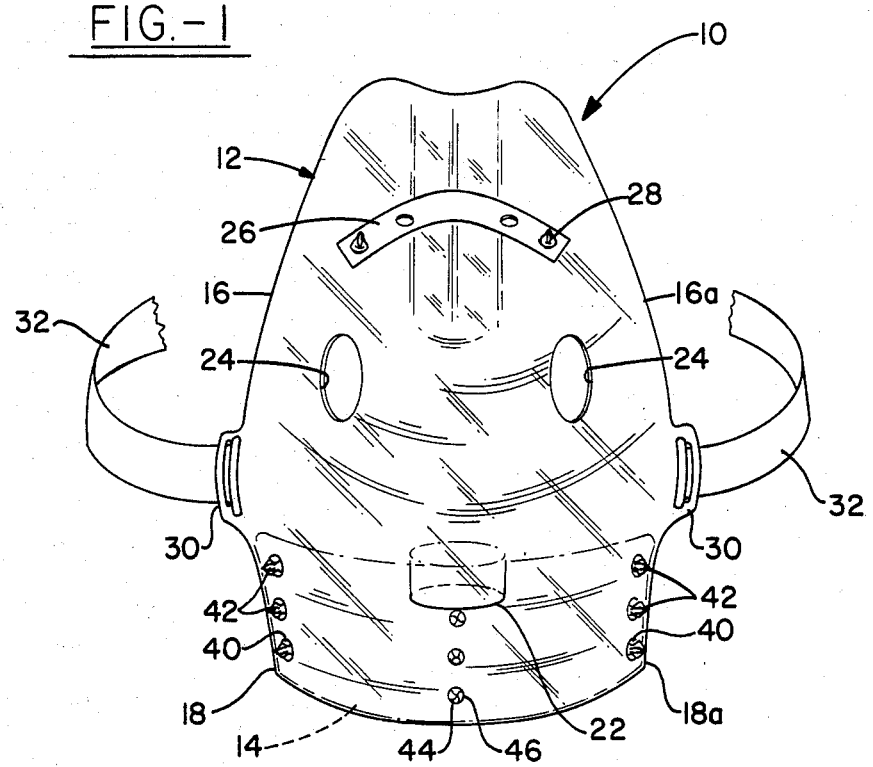
FIG. 1 is a front view of the mask according to one embodiment of this invention.
Figures 2, 3:
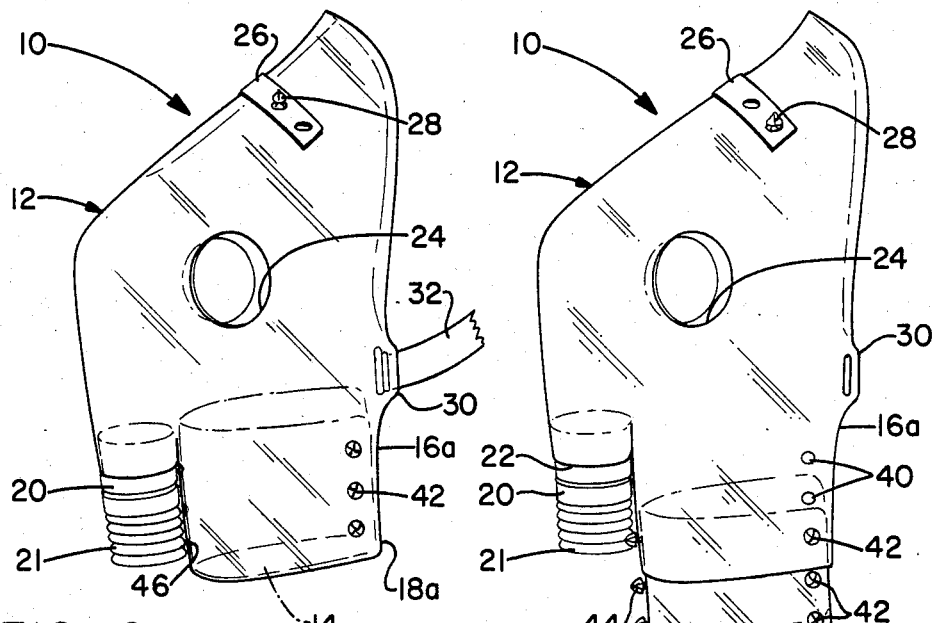
FIG. 2 is a side view of the mask according to the embodiment of FIG. 1, adjusted to fit an adult of small size.
FIG. 3 is a side view of the mask according to the embodiment of FIG. 1, adjusted for a larger adult.

This invention will now be described in detail in the reference to one embodiment thereof, as shown in FIGS. 1-3 of the drawings. The mask of this embodiment is an adjustable oxygen mask.

Referring now to FIGS. 1 and 2, 10 is an adjustable oxygen mask according to a first embodiment of the invention. Mask 10 has overlapping upper and lower sections 12 and 14, respectively. Upper section 12 preferably fits over lower section 14 as shown. That is, upper section 12 is normally the outside section and lower section 14 is normally the inside section (the section closest to the wearer's face) in the area of overlap, although the reverse can be the case. Both sections are made of a flexible airtight material, as for example a thin sheet of flexible plastic or rubber. The plastic sheet material is usually clear. The two mask sections 12 and 14 together are adapted to cover the face of a wearer and to form an airtight enclosure with the wearer's face. The lateral edges 16, 16a of upper section 12 and the lateral edges 18, 18a of lower section 14 fit tightly against the sides of the wearer's face so as to form the desired airtight enclosure. The two sections 12, 14 of mask 10 are aligned so that the lateral edges 18, 18a of lower section 14 are in effect continuations of the lateral edges 16, 16a, respectively, of upper section 12.

An open-ended tubular connection 20, for attachment of a flexible hose 21 for supplying oxygen or other desired atmosphere (e.g. oxygen enriched air) to the wearer of mask 10, is joined to upper mask section 12 along closed curved line 22. (FIG. 1) Tubular connection 20 is open at both ends and is preferably rigid. The flexible hose (not shown) may be a conventional flexible hose for supplying oxygen. Tubular connection 20 has been omitted in FIG. 1 for the sake of clarity.

Upper section 12 also has a pair of exhalation holes or exhaust ports 24 for air exhaled by the wearer. At least one exhaust port must be provided.

A strap 26 having a plurality of spaced fasteners 28 is provided above exhaust ports 24, i.e. at the bridge of the nose, on the upper section 12 of mask 10 for adjusting the mask to fit the facial width of the wearer.

Mask 10 also has a pair of ears 30 (FIG. 1) along the lateral edges thereof for receiving a strap 32. Strap 32 extends around the back of the wearer's head and thereby holds the mask 10 in place. Strap 32 may be similar to those used to secure present day oxygen masks to the wearer. Alternatively and preferably, the two ends of strap 32 are self-adhesive, e.g. "Velcro" and the middle portion (which is preferably elastic) may be of any desired fabric, e.g. cotton. This preferred strap is comfortable and is readily adjustable to fit the head size of the wearer.

Upper and lower sections 12 and 14, respectively, of mask 10 are secured together in overlapping relationship. To this end, sections 12 and 14 have coacting gripping means. Upper section 12, which is the outside section as shown, has first gripping means in the form of a plurality of eyelets 40 arranged in two rows, one along each of the lateral edges 16, 16a in the lower portion of upper section 12. Lower section 14, which is the side section as shown, has second gripping means in the form of a plurality of outwardly extending snaps 42. In other words, both sections 12 and 14 are provided with gripping means in the area of overlap. Snaps 42 are also arranged in two rows, one along each of the lateral edges 18, 18a in the upper portion of lower section 14. Snaps 42 are capable of being received in eyelets 40, so that the two mask sections 12 and 14 may be secured together with any desired amount of overlap in accordance with the facial dimensions of the wearer of mask 10. In the specific embodiment shown, both eyelets 40 and snaps 42 are arranged in two rows of three snaps or eyelets each. Of course, the snaps 42 in a row, and the eyelets 40 in a row, must be uniformly spaced apart by the same amount so that the desired coaction between the snaps 42 and eyelets 40 is obtained.

Upper section 12 has an additional row of eyelets 44 in the lower portion thereof, and lower section 14 may have an additional row of snaps 46 in the upper portion thereof. These additional rows extend vertically along the centerlines of the respective sections. These additional snaps and eyelets help to keep the two mask sections together so as to assure an airtight closure.

It will be understood that upper section 12 can be the inside section and lower section 14 the outside section if desired. In this case it is preferable that the upper section 12 be provided with snaps 42 and lower section 14 with eyelets 40. The snaps 42 are preferably always carried by the inside section.

FIGS. 1 and 2 show the two sections 12 and 14 of mask 10 positioned for a small adult, i.e. one having a face of less than average depth. All three snaps 42 in each row engage eyelets 40 in the corresponding row, so that there are no free snaps or eyelets.

FIG. 3 shows the two sections 12 and 14 of mask 10 positioned for a large adult, i.e. one of greater than average facial depth. Only one snap 42 (i.e. the uppermost snap) in each row engages an eyelet 40 (i.e. the lowermost eyelet in each row).

The two sections 12 and 14 of mask 10 may also be positioned to fit an average adult (i.e. one of average facial length). In this instance, two snaps 42 in each row engage an eyelet, so that the uppermost eyelet 40 and the lowermost snap 42 in each row are free.

Other forms of gripping means may be used instead of the snaps and eyelets shown. For instance, upper section 12 and lower section 14 may be provided with "Velcro" closures in the form of strips extending along the lateral edges 16, 16a and 18, 18a of the respective sections 12 and 14. The "Velcro" closure strips may be placed in the same positions as the rows of snaps and eyelets shown in FIGS. 1-3. The "Velcro" strips on upper section 12 engage the corresponding "Velcro" strips on lower section 14 to secure the two sections together.

It is possible to provide "Velcro" strips on only one of the two sections 12 and 14, since a "Velcro" strip will effectively grip the other section either directly or through another "Velcro" strip.

Regardless of the form of gripping means used, it is always preferable to place the gripping means along the lateral edges of the section or sections 12 and 14 having such means.

A second embodiment of this invention will now be described with reference to FIGS. 4–7. The mask of this embodiment is particularly useful for preventing dust or pollen from reaching the wearer.

Figure 4:
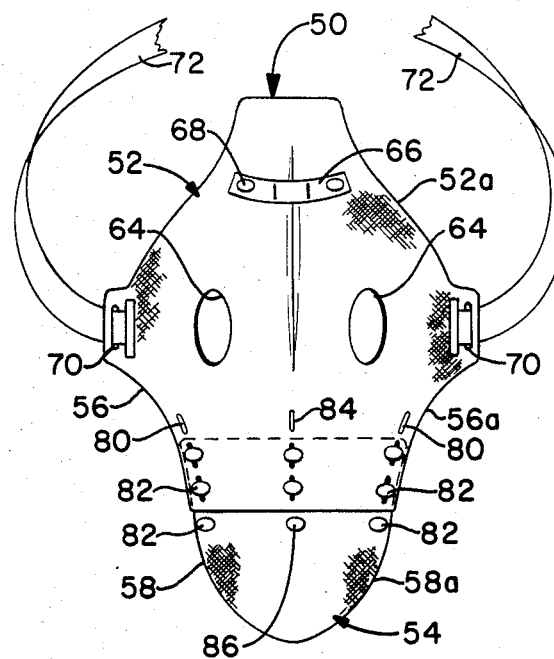
FIG. 4 is a front view of the mask according to another embodiment of this invention.
Figure 5:
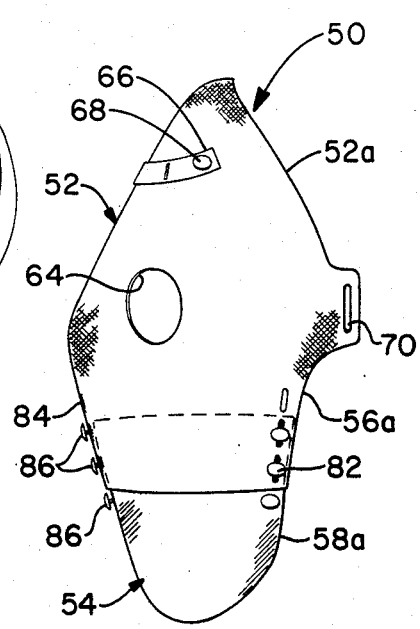
FIG. 5 is a side view of the mask according to the embodiment of FIG. 4, adjusted to fit an adult of average size.

Referring to FIGS. 4 and 5, 50 is an adjustable mask for filtering out dust and pollen so that only a desired dust and pollen-free atmosphere will reach the wearer. Mask 50 has overlapping upper and lower sections 52 and 54, respectively. Upper section 52 preferably fits over lower section 54 as shown. Both sections 52 and 54 are made of a flexible fine mesh material, such as cotton with reinforced edges, or plastic. The two mask sections 52 and 54 together are adapted to cover the face of the wearer. The fine mesh openings in both sections filter out dust and pollen particles while permitting air to pass through. The lateral edges 58, 58a grip the wearer's face, forming an airtight seal so that all air which enters the enclosure between the mask 50 and the wearer's face must pass through the fine mesh openings. The sections 52, 54 are aligned so that the lateral edges 58, 58a of the lower section 54 are in effect continuations of the lateral edges 52, 52a, respectively, of upper section 52.

Upper section 52 has a pair of openings 64 which form exhaust ports for air exhaled by the wearer.

A strap 66 having a plurality of spaced fasteners 68 is provided above openings 64, i.e. at top of nose height, on the upper section 52 of mask 50.

Mask 50 also has a pair of ears 70 along the lateral edges thereof for receiving a strap 72 (FIG. 4). Strap 72 extends around the back of the wearer's head and thereby holds the mask 50 in place. Strap 72 may be similar to strap 32 in the embodiment of FIGS. 1-3.

Upper and lower sections 52 and 54, respectively, of mask 50 are secured together in overlapping relationship. To this end, sections 52 and 54 have coacting gripping means. These gripping means may be identical or similar to the gripping means in the embodiment of FIGS. 1-3. Thus, the lower portion of upper section 52 has first gripping means in the form of a plurality of eyelets 80 (six are shown), and the upper portion of lower section 54 has a second gripping means in the form of a plurality of snaps 82 (six are shown) which are received in the eyelets 80. Both the eyelets 80 and the snaps 82 are arranged in two rows along the respective lateral edges 56, 56a and 58, 58a of upper and lower sections 52 and 54, respectively. An additional row of eyelets 84 and snaps 86, extending along the centerline of mask 50, is included. The eyelets 80, 84 and snaps 82, 86 may be replaced by "Velcro" closure strips or other suitable gripping means, as described with respect to FIGS. 1-3, if desired.

The upper and lower sections 52 and 54, respectively, may be positioned relative to each other to fit a small, average or large adult. This adjustment or relative positioning is achieved in the manner described in connection with the embodiment of FIGS. 1-3.

FIGS. 4 and 5 show the mask 50 adjusted to fit an average adult. In this position two snaps 2 in each row engage two eyelets.

Figure 6:
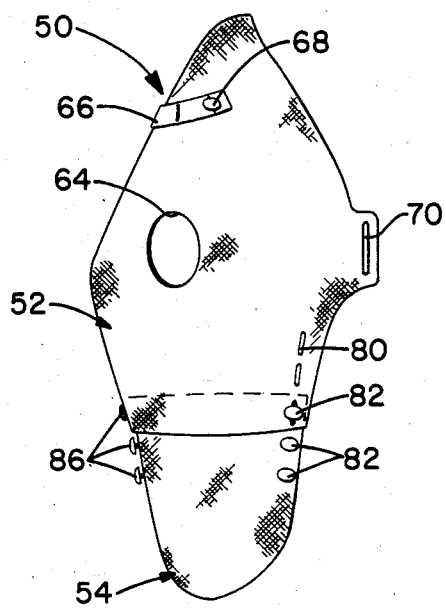
FIG. 6 is a side view of the mask according to the embodiment of FIG. 4, adjusted for a larger adult.

FIG. 6 shows the mask adjusted for a large adult. In this position the overlap between sections 52 and 54 is minimal and only one snap 82 in each row engages an eyelet 80.

Figure 7:
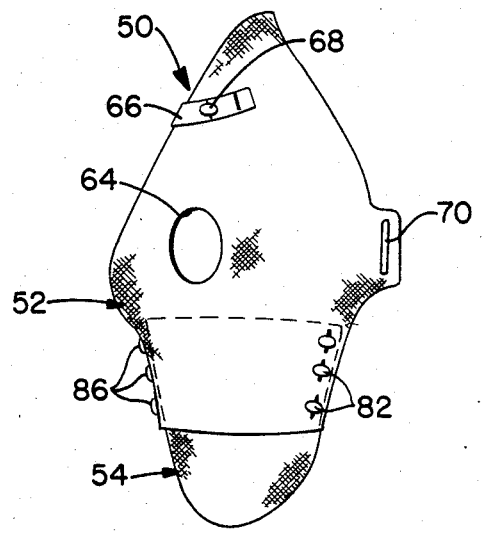
FIG. 7 is a side view of the mask according to the embodiment of FIG. 4, adjusted for a smaller adult.

FIG. 7 shows the mask adjusted for a small adult. In this case the area of overlap between the sections 52 and 54 is at a maximum and all three snaps 82 in each row engage eyelets.

While this invention has been described with particular reference to adult masks, the same principle applies to children's masks. Thus, one size of mask (smaller than the adult size) will fit children over a wide range of ages. The mask adjusted to its shortest length fits younger children, and the same mask adjusted to intermediate or longer length fits older children.

One size of mask, constructed according to the present invention, will fit all or most adults. This assures a good fit in most cases. Similarly, masks which will fit most children can be provided without the necessity of a large number of sizes.

While in accordance with the patent statutes, a preferred embodiment and best mode has been presented, the scope of the invention is not limited thereto, but rather is measured by the scope of the attached claims.

What is claimed is:

1. An adjustable mask for supplying a desired atmosphere to the wearer, said mask comprising separate overlapping flexible upper and lower sections, said upper section having a lower portion in overlapping engagement with the upper portion of said lower section, said upper and lower sections being vertically adjustable with respect to each other and which together defined a peripheral edge adapted to cover the wearer's face and to form an enclosure therewith, one of said sections being inside the other in the area of overlap, the amount of overlap between said upper and lower sections being adjustable in accordance with the height of the wearer's face, means for transferring a gas to and from said enclosure, and means for adjustably securing the two sections together in overlapping relationship, said means comprising, gripping means carried by at least one of said sections in the portion that overlaps the other, said gripping means being capable of maintaining the two sections in a plurality of different positions relative to each other so that the mask can be made larger or smaller in accordance with the facial dimensions of the wearer.

2. A mask according to claim 1 in which said gripping means are disposed along the lateral edges of at least one of said sections.

3. A mask according to claim 1 wherein said gripping means comprises first gripping means along the lateral edges of said upper section on the lower portion thereof and second gripping means along the lateral edges of said lower section in the upper portion thereof, said first and second gripping means being capable of coacting with each other to maintain the two sections in said plurality of different positions.

4. A mask according to claim 3 in which said first gripping means comprises a plurality of eyelets arranged in rows in the outside section, and said second gripping means comprises a plurality of snaps arranged in rows in the inside section, said snaps being capable of coacting with said eyelets to hold the two sections together in a desired relative position.

5. A mask according to claim 4 wherein the upper section is the outside section and the lower section is the inside section.

6. An adjustable mask according to claim 1 wherein one of said gripping means includes a plurality of spaced eyelets along each lateral edge and the other of said gripping means includes a plurality of members capable of engaging said eyelets so as to hold the two sections together in a predetermined relationship.

7. A mask according to claim 6 in which said first gripping means comprises said eyelets and said second gripping means comprises said members capable of engaging said eyelets.

8. A mask according to claim 1, wherein said mask is an oxygen mask and wherein said gas transferring means comprises an open-ended tubular connection for an oxygen supply hose joined to the upper section of the mask, and at least one exhaust port for air exhaled by the wearer.

9. A mask according to claim 1, wherein said mask is a mask for removing dust or pollen, and wherein said gas transferring means comprises fine mesh openings for filtering out dust and pollen particles while permitting air to pass through.

10. A mask according to claim 1 wherein the lateral edges of said mask are adapted to fit tightly against the face of the wearer.

11. A mask according to claim 1, further including means in said upper section for adjusting the mask in accordance with the width of the wearer's face.

12. A mask according to claim 1, further including a strap secured to said upper section and adapted to extend around the head of the wearer.

* * * * *